(12) United States Patent
Helal et al.

(10) Patent No.: US 11,498,906 B1
(45) Date of Patent: Nov. 15, 2022

(54) METHOD OF FIXATING CARBON DIOXIDE TO SUBSTITUTED OXAZOLIDINONES

(71) Applicant: King Fahd University of Petroleum and Minerals, Dhahran (SA)

(72) Inventors: Aasif Helal, Dhahran (SA); Muhammad Usman, Dhahran (SA); Mahmoud Mohamed Abdelnaby, Dhahran (SA); Md. Eyasin Arafat, Dhahran (SA)

(73) Assignee: King Fahd University of Petroleum and Minerals, Dhahran (SA)

( * ) Notice: Subject to any disclaimer, the term of this patent is extended or adjusted under 35 U.S.C. 154(b) by 2 days.

(21) Appl. No.: 17/728,514

(22) Filed: Apr. 25, 2022

(51) Int. Cl.
| | |
|---|---|
| *C07D 263/22* | (2006.01) |
| *B01J 31/16* | (2006.01) |
| *B01J 31/02* | (2006.01) |
| *C07D 263/52* | (2006.01) |
| *C07D 263/24* | (2006.01) |

(52) U.S. Cl.
CPC ........ *C07D 263/22* (2013.01); *B01J 31/0271* (2013.01); *B01J 31/1691* (2013.01); *C07D 263/24* (2013.01); *C07D 263/52* (2013.01); *B01J 2231/328* (2013.01); *B01J 2531/48* (2013.01)

(58) Field of Classification Search
None
See application file for complete search history.

(56) References Cited

U.S. PATENT DOCUMENTS

| | | |
|---|---|---|
| 10,233,145 B2 | 3/2019 | Farha et al. |
| 10,413,858 B2 | 9/2019 | Mu et al. |
| 11,185,843 B2 | 11/2021 | Usman et al. |

FOREIGN PATENT DOCUMENTS

| | | |
|---|---|---|
| CN | 111013661 A | 4/2020 |
| CN | 113000070 A | 6/2021 |

OTHER PUBLICATIONS

Helal et al. "Allyl functionalized UiO-66 metal-organic framework as a catalyst for the synthesis of cyclic carbonates by CO2 cycloaddition" Journal of Industrial and Engineering Chemistry, 2020, vol. 89, pp. 104-110.*

Delavari, et al. ; Catalytic synthesis of cyclic carbonates from epoxides and carbon dioxide by magnetic UiO-66 under mild conditions ; Applied Organometallic Chemistry ; Abstract Only, 2017, vol. 31, No. 7, e3656.

Helal, et al. ; Defect-engineering a metal-organic framework for CO2 fixation in the synthesis of bioactive oxazolidinones ; Inorganic Chemistry Frontiers ; Aug. 6, 2020, vol. 7, pp. 3571-3577.

* cited by examiner

*Primary Examiner* — Joseph R Kosack
(74) *Attorney, Agent, or Firm* — Oblon, McClelland, Maier & Neustadt, L.L.P.

(57) ABSTRACT

A method of fixating carbon dioxide ($CO_2$) to a substituted oxazolidinone. The method includes mixing a metal-organic framework (MOF), a co-catalyst, at least one para-substituted aromatic amine, and at least one epoxide to form a mixture. The method further includes contacting the mixture with a gas stream containing $CO_2$ to react the $CO_2$ in the gas stream with the epoxide and para-substituted aromatic amine to form a substituted oxazolidinone mixture. The MOF is a UiO-66-X MOF, where X is of formula (I) wherein at least one of $R^1$ to $R^4$ is an allyloxy group, and $R^1$ to $R^4$ are independently an allyloxy group or a hydrogen.

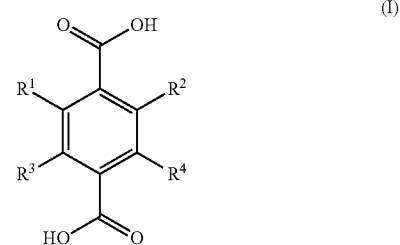

(I)

19 Claims, 7 Drawing Sheets

METHOD OF FIXATING CARBON DIOXIDE TO SUBSTITUTED OXAZOLIDINONES

BACKGROUND

Technical Field

The present disclosure is directed to a method of fixating carbon dioxide ($CO_2$), and particularly to a method of fixating $CO_2$ to a substituted oxazolidinone.

Description of Related Art

The "background" description provided herein is for the purpose of generally presenting the context of the disclosure. Work of the presently named inventors, to the extent it is described in this background section, as well as aspects of the description which may not otherwise qualify as prior art at the time of filing, are neither expressly nor impliedly admitted as prior art against the present invention.

Extensive use of fossil fuels as a primary source of energy in vehicles and industries has steadily increased carbon dioxide ($CO_2$) levels in the atmosphere, resulting in abnormal global climate change. Currently, several homogeneous catalysts such as quaternary ammonium salts, ionic liquids, transitional metal complexes, and organo-catalysts have been used to convert the $CO_2$ gas into value-added products, a method known as $CO_2$ fixation. However, such homogeneous catalysts include drawbacks such as recyclability, separation of catalysts, and purification of final products.

One product that can be generated through $CO_2$ fixation is an oxazolidinone, which are highly important five-membered heterocyclic compounds containing nitrogen and oxygen. They are extensively used as an intermediate in organic synthesis of antibacterial, and antimicrobial agents such as tedizolid, linezolid, and radezolid, and also as a key structural unit in pharmaceutical and agrochemical industries. Thus, methods have been developed for the synthesis of oxazolidinones, however most of these methods use carbon dioxide under high pressure, expensive metal catalysts, and are non-recyclable. Hence, efficient methods need to be developed, which may substantially reduce or eliminate the above limitations.

SUMMARY

In an exemplary embodiment, a method of fixating carbon dioxide ($CO_2$) to a substituted oxazolidinone is described. The method includes mixing a metal-organic framework (MOF), a co-catalyst, at least one para-substituted aromatic amine, and at least one epoxide to form a mixture. The method further includes contacting the mixture with a gas stream containing $CO_2$ to react the $CO_2$ in the gas stream with the at epoxide and the para-substituted aromatic amine to form a substituted oxazolidinone mixture. The MOF is a UiO-66-X MOF, where X is of formula (I):

(I)

and where, at least one of $R^1$ to $R^4$ is an allyloxy group, and $R^1$ to $R^4$ are independently an allyloxy group or hydrogen.

In some embodiments, X is:

In some embodiments, the MOF has a surface area is 450-550 square meter per gram ($m^2/g$).

In some embodiments, the MOF has a pore size of 1.0-1.5 nanometers (nm).

In some embodiments, the MOF has a $CO_2$ uptake capacity of 75-90 cubic centimeter per gram ($cm^3/g$) at 273 kelvin (K), 40-60 $cm^3/g$ at 298 K, and 20-35 $cm^3/g$ at 313 K, each at 800 torr.

In some embodiments, the epoxide is at least one selected from a group including 1,2-epoxypropane, 1,2-epoxybutane, 1,2-epoxyhexane, styrene oxide, allyl glycidyl ether, and phenyl glycidyl ether.

In some embodiments, the para-substituted aromatic amine is at least one selected from a group including aniline, 4-chloroaniline, 4-nitroaniline, toluidine, para-anisidine, and 4-aminothiophenol.

In some embodiments, the co-catalyst is selected from a group including tetrabutylammonium iodide (TBAI), tetrabutylammonium bromide (TBAB), and tetrabutylammonium fluoride (TBAF).

In some embodiments, the mixture has a 1 to 100-500 molar ratio of the co-catalyst to the MOF.

In some embodiments, the mixture has a 1 to 1-5 molar ratio of the MOF to the para-substituted aromatic amine.

In some embodiments, the para-substituted aromatic amine is adsorbed to a solid support in the mixture.

In some embodiments, the solid support is selected from a group including silica gel, alumina, and a polymeric support.

In some embodiments, the method includes contacting the mixture with the gas stream at a temperature of 30-100 degrees Celsius (° C.) to form the substituted oxazolidinone mixture.

In some embodiments, the method includes contacting the mixture with the gas stream at a pressure of 1-15 bar of the $CO_2$ to form the substituted oxazolidinone mixture.

In some embodiments, the method includes contacting the mixture with the gas stream for 5-20 hours to form the substituted oxazolidinone mixture.

In some embodiments, 75-99% of the para-substituted aromatic amine is converted into the substituted oxazolidinone.

In some embodiments, the substituted oxazolidinone is of formula (II):

(II)

where, X is selected from a group including an alkyl chain, an allyloxy group, a halogen substituted alkyl chain, and a substituted aromatic group, Y is selected from a group including hydrogen, a halogen, a nitro group, an alkyl chain, a methoxy group, and a thiol.

In some embodiments, the method further includes adding a polar solvent to the substituted oxazolidinone mixture, centrifuging, and filtering to separate recovered MOF. The method further includes washing the recovered MOF with an organochloride solvent and drying at a temperature of 130-160° C. for at least 5 hours to separate recycled MOF.

In some embodiments, the MOF maintains catalytic activity after it is recycled up to 9 times.

The foregoing general description of the illustrative present disclosure and the following detailed description thereof are merely exemplary aspects of the teachings of this disclosure and are not restrictive.

BRIEF DESCRIPTION OF THE DRAWINGS

A more complete appreciation of this disclosure and many of the attendant advantages thereof will be readily obtained as the same becomes better understood by reference to the following detailed description when considered in connection with the accompanying drawings, wherein.

DETAILED DESCRIPTION

In the drawings, like reference numerals designate identical or corresponding parts throughout the several views. Further, as used herein, the words "a," "an" and the like generally carry a meaning of "one or more," unless stated otherwise.

Furthermore, the terms "approximately," "approximate," "about," and similar terms generally refer to ranges that include the identified value within a margin of 20%, 10%, or preferably 5%, and any values there between.

As used herein, the terms "optional" or "optionally" means that the subsequently described event(s) can or cannot occur or the subsequently described component(s) may or may not be present (e.g., 0 wt. %).

The term "alkyl", as used herein, unless otherwise specified, refers to a straight, branched, or cyclic, saturated aliphatic fragment having 1 to 26 carbon atoms, (e.g., $C_1$, $C_2$, $C_3$, $C_4$, $C_5$, $C_6$, $C_7$, $C_8$, $C_9$, $C_{10}$, $C_{11}$, etc.) and specifically includes, but is not limited to, methyl, ethyl, propyl, isopropyl, butyl, isobutyl, t-butyl, pentyl, isopentyl, neopentyl, hexyl, isohexyl, 3-methylpentyl, 2,2-dimethylbutyl, 2,3-dimethylbutyl, 2-ethylhexyl, heptyl, octyl, nonyl, 3,7-dimethyloctyl, decyl, undecyl, dodecyl, tridecyl, tetradecyl, pentadecyl, hexadecyl, heptadecyl, octadecyl, nonadecyl, eicosyl, guerbet-type alkyl groups (e.g., 2-methylpentyl, 2-ethylhexyl, 2-propylheptyl, 2-butyloctyl, 2-pentylnonyl, 2-hexyldecyl, 2-heptylundecyl, 2-octyldodecyl, 2-nonyltridecyl, 2-decyltetradecyl, and 2-undecylpentadecyl), as well as cyclic alkyl groups (cycloalkyls) such as cyclopropyl, cyclobutyl, cyclopentyl, cyclohexyl, norbornyl, and adamantyl.

The term "aryl" means a carbocyclic aromatic monocyclic group containing 6 carbon atoms which may be further fused to a second 5- or 6-membered carbocyclic group which may be aromatic, saturated or unsaturated. Aryl includes, but is not limited to, phenyl, anthracenyl, indanyl, 1-naphthyl, 2-naphthyl, and tetrahydronaphthyl. The fused aryls may be connected to another group either at a suitable position on the cycloalkyl/cycloalkenyl ring or the aromatic ring.

The term "arylalkyl", as used herein, refers to a straight or branched chain alkyl moiety (as defined above) that is substituted by an aryl group (as defined above), examples of which include, but are not limited to, benzyl, phenethyl, 2-methylbenzyl, 3-methylbenzyl, 4-methylbenzyl, 2,4-dimethylbenzyl, 2-(4-ethylphenyl)ethyl, 3 -(3-propylphenyl) propyl, and the like.

The term "allyloxy", as used herein, unless otherwise specified, refers to an —O—CH$_2$—CH═CH$_2$ group.

The term "epoxide", as used herein, unless otherwise specified, refers to a cyclic ether with a three-atom ring.

The term "oxazolidinone", as used herein, unless otherwise specified, is a heterocyclic organic compound containing both nitrogen and oxygen in a 5-membered ring.

As used herein, the term "substituted" refers to at least one hydrogen atom that is replaced with a non-hydrogen group, provided that normal valencies are maintained and that the substitution results in a stable compound. When a substituent is noted as "optionally substituted", the substituent(s) are selected from alkyl, halo (e.g., chloro, bromo, iodo, fluoro), hydroxyl, alkoxy, oxo, alkanoyl, aryloxy, alkanoyloxy, amino (—$NH_2$), alkylamino (—NHalkyl), cycloalkylamino (—NHcycloalkyl), arylamino (—NHaryl), arylalkylamino (—NHarylalkyl), disubstituted amino (e.g., in which the two amino substituents are selected from alkyl, aryl or arylalkyl, including substituted variants thereof, with specific mention being made to dimethylamino), alkanoylamino, aroylamino, arylalkanoylamino, thiol, alkylthio, arylthio, arylalkylthio, alkylthiono, arylthiono, arylalkylthiono, alkyl sulfonyl, aryl sulfonyl, arylalkylsulfonyl, sulfonamide (e.g., —SO2NH2), substituted sulfonamide (e.g., —$SO_2$NHalkyl, —$SO_2$NHaryl, —$SO_2$NHarylalkyl, or cases where there are two substituents on one nitrogen selected from alkyl, aryl, or alkylalkyl), nitro, cyano, carboxy, unsubstituted amide (i.e. $CONH_2$), substituted amide (e.g., —CONHalkyl, —CONHaryl, —CONHarylalkyl or cases where there are two substituents on one nitrogen selected from alkyl, aryl, or alkylalkyl), alkoxycarbonyl, aryl, guanidine, heterocyclyl (e.g., pyridyl, furyl, morpholinyl, pyrrolidinyl, piperazinyl, indolyl, imidazolyl, thienyl, thiazolyl, pyrrolidyl, pyrimidyl, piperidinyl, homopiperazinyl), and mixtures thereof. The substituents may themselves be optionally substituted, and may be either unprotected, or protected as necessary, as known to those skilled in the art.

Throughout the specification and the appended claims, a given chemical formula or name shall encompass all isomers (stereo and optical isomers and racemates) thereof where such isomers exist. Unless otherwise indicated, all chiral (enantiomeric and diastereomeric) and racemic forms are within the scope of the disclosure. Many geometric isomers of C=C double bonds, C=N double bonds, ring systems, and the like can also be present in the compounds, and all such stable isomers are contemplated in the present disclosure. Cis- and trans- (or E- and Z-) geometric isomers of the compounds of the present disclosure are described and may be isolated as a mixture of isomers or as separated isomeric forms. The present compounds can be isolated in optically active or racemic forms. Optically active forms may be prepared by resolution of racemic forms or by synthesis from optically active starting materials. All processes used to prepare compounds of the present disclosure and intermediates made therein are considered to be part of the present disclosure. When enantiomeric or diastereomeric products are prepared, they may be separated by conventional methods, for example, by chromatography, fractional crystallization, or through the use of a chiral agent. Depending on the process conditions the end products of the present disclosure are obtained either in free (neutral) or salt form. Both the free form and the salts of these end products are within the scope of the disclosure. If so desired, one form of a compound may be converted into another form. A free base or acid may be converted into a salt; a salt may be converted into the free compound or another salt; a mixture of isomeric compounds of the present disclosure may be separated into the individual isomers. Compounds of the present disclosure, free form and salts thereof, may exist in multiple tautomeric forms, in which hydrogen atoms are transposed to other parts of the molecules and the chemical bonds between the atoms of the molecules are consequently rearranged. It should be understood that all tautomeric forms, insofar as they may exist, are included within the disclosure. Further, a given chemical formula or name shall encompass all conformers, rotamers, or conformational isomers thereof where such isomers exist. Different conformations can have different energies, can usually interconvert, and are very rarely isolatable. There are some molecules that can be isolated in several conformations. For example, atropisomers are isomers resulting from hindered rotation about single bonds where the steric strain barrier to rotation is high enough to allow for the isolation of the conformers. It should be understood that all conformers, rotamers, or conformational isomer forms, insofar as they may exist, are included within the present disclosure.

As used herein "metal-organic frameworks" or MOFs are compounds having a lattice structure made from (i) a cluster of metal ions as vertices ("cornerstones")("secondary building units" or SBUs) which are metal-based inorganic groups, for example metal oxides and/or hydroxides, linked together by (ii) organic linkers. The linkers are usually at least bidentate ligands which coordinate to the metal-based inorganic groups via functional groups such as carboxylates and/or amines. MOFs are considered coordination polymers made up of (i) the metal ion clusters and (ii) linker building blocks.

Aspects of the present invention are directed towards the synthesis and characterization of a bisallyloxy derivatized UiO-66 nanocrystalline metal-organic framework (MOF) or herein referred to as the "MOF", and its application in catalysis by $CO_2$ fixation. The catalytic activity of the MOF in two types of conversions, (i) epoxides to cyclic carbonates and (ii) epoxides in presence of aromatic amines to oxazolidinones, in presence of $CO_2$, are described. Results show that the bisallyloxy derivatized UiO-66 nanocrystalline MOF provides efficient separation, better sample handling, and reusability in comparison to the conventionally used catalysts.

Figure 1:
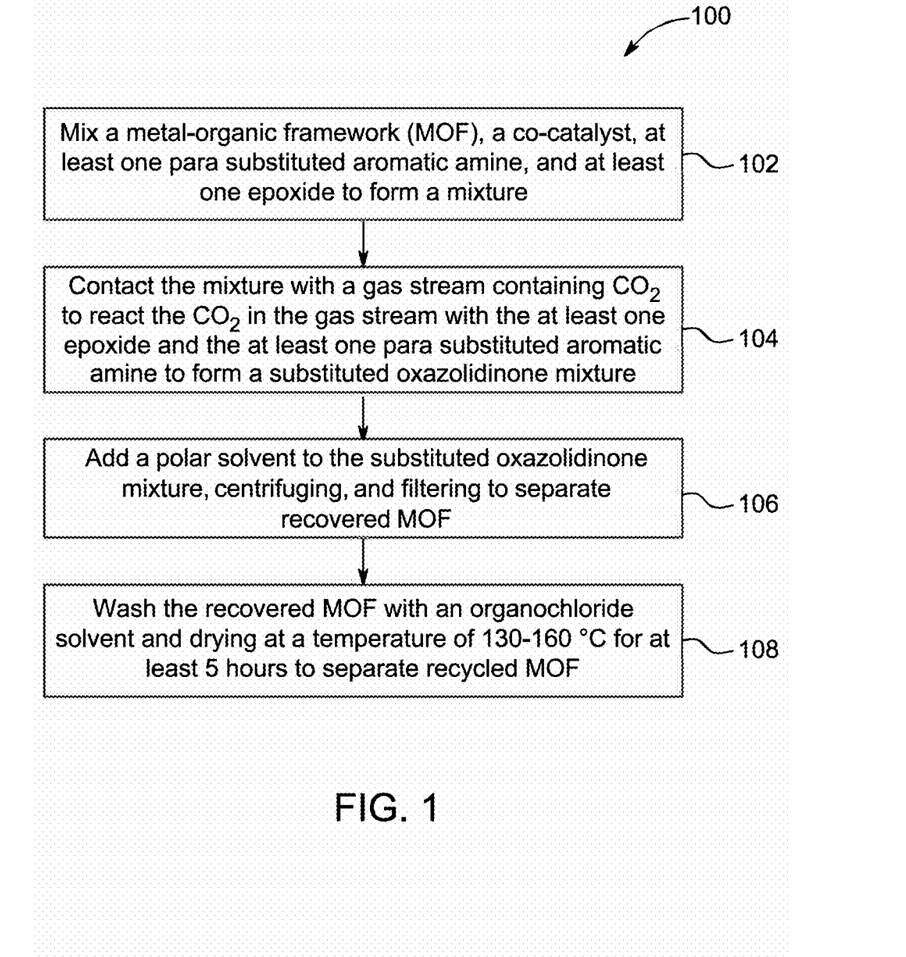
FIG. 1 is a flow chart of a method of fixating $CO_2$ to a substituted oxazolidinone, according to embodiments of the present disclosure.

FIG. 1 illustrates a flow chart of a method 100 of fixating $CO_2$ to a substituted oxazolidinone. The order in which the steps of the method 100 is described is not intended to be construed as a limitation, and any number of the described method steps can be combined in any order to implement the method 100. Additionally, individual steps may be removed or skipped from the method 100 without departing from the spirit and scope of the present disclosure.

At step 102, the method 100 includes mixing a MOF, a co-catalyst, one or more para-substituted aromatic amines, and one or more epoxides to form a mixture. In some embodiments, the MOF may be any zirconium-based MOF. The MOF of the present disclosure is preferably based on zirconium ions (made from zirconium ion clusters), referred to herein as a zirconium metal-organic framework (Zr-MOF). The Zr-MOF herein is intended to cover any MOF which contains predominantly zirconium ions with respect to the total metal ion content. The Zr-MOFs of the disclosure include zirconium ion clusters (cornerstones) which are zirconium inorganic groups, typically zirconium ions connected by bridging oxygen groups, bridging hydroxide groups, or both. These zirconium ion clusters are further coordinated to at least one linker. In some cases, the zirconium ion clusters may be further connected to non-bridging modulator species, complexing reagents or ligands (e.g., sulfates or carboxylates such as formate, benzoate, acetate, etc.) and/or solvent molecules (e.g., H2O). The idealized zirconium ion cluster is considered to be a hexanuclear zirconium ion cluster based on an octahedron of zirconium ions ($Zr^{4+}$) which are µ3-bridged by $O_2$— and/or OH— ions via the faces of the octahedron and further saturated by coordinating ligands containing oxygen atoms like carboxylate groups. Preferably, each zirconium ion cluster is coordinated by between 6 and 12 carboxylate groups, or between 8 and 11 carboxylate groups, or 10 carboxylate groups (preferentially as close as possible to 12 carboxylate groups), the carboxylate groups being from the linker and/or a modulator. However, in practice, there is a degree of flexibility in the structure of the zirconium ion cluster.

In addition to the zirconium ion clusters (cornerstones), the Zr-MOFs of the present disclosure are formed from at least one linker, which may be bidentate, tridentate, or tetradentate, and which links together adjacent zirconium ion clusters to form the coordinated network. In preferred embodiments, the linker is of formula (I). In some embodiments, the MOF is a UiO-66-X MOF, where X is of formula (I):

One or more of $R^1$ to $R^4$ is an allyloxy group, and $R^1$ to $R^4$ are independently an allyloxy group or a hydrogen. In some embodiments, three of $R^1$ to $R^4$ are allyloxy groups, and one is a hydrogen. In some embodiments, three of $R^1$ to $R^4$ are hydrogens, and one is an allyloxy group. In some embodiments, $R^1$ and $R^2$ are allyloxy groups and $R^3$ and $R^4$ are hydrogens. In some embodiments, $R^2$ and $R^3$ are allyloxy groups and $R^1$ and $R^4$ are hydrogens (depicted below).

In some embodiments, X is:

In some embodiments, the MOF has a BET surface area of 300 to 600 $m^2/g$, preferably 320 to 580 $m^2/g$, preferably 340 to 560 $m^2/g$, preferably 360 to 540 $m^2/g$, preferably 380 to 520 $m^2/g$, preferably 400 to 500 $m^2/g$, preferably 440 to 490 $m^2/g$, preferably 486 $m^2/g$. In some embodiments, the MOF may have a pore size of 1.0-1.5 nm, preferably 1.1-1.4 nm, or 1.2-1.3 nm. Both the surface area and pore size of the MOF of the present disclosure are significantly smaller than those reported for UiO-66 due to the presence of the allyloxy group(s) in the pores.

The MOF of the present disclosure has an effective adsorption capacity for $CO_2$. In some embodiments, the MOF may have a $CO_2$ uptake capacity of 75-90 $cm^3/g$, preferably 77 to 88 $cm^3/g$, preferably 79 to 86 $cm^3/g$, preferably 81 to 84 $cm^3/g$, preferably 83 to 83.5 $cm^3/g$ at 273 K and 800 Torr. In some embodiments, the MOF may have a $CO_2$ uptake capacity of 40 to 60 $cm^3/g$, preferably 42 to 58 $cm^3/g$, preferably 44 to 56 $cm^3/g$, preferably 46 to 54 $cm^3/g$, preferably 48 to 52 $cm^3/g$, preferably 50 to 51 $cm^3/g$ at 298 K and 800 Torr. In some embodiments, the MOF may have a $CO_2$ uptake capacity of 20 to 35 $cm^3/g$, preferably 22 to 33 $cm^3/g$, preferably 24 to 31 $cm^3/g$, preferably 26 to 29 $cm^3/g$, at 313 K and 800 Torr. In some embodiments, the MOF is stable up to 425° C., preferably 100-425° C., 200-400° C., or 300-350° C.

In some embodiments, the epoxide is any epoxide known in the art substituted at only one carbon of the three membered ring. In some embodiments, the epoxide is one or more selected from a group including 1,2-epoxypropane, 1,2-epoxybutane, 1,2-epoxyhexane, styrene oxide, allyl glycidyl ether, and phenyl glycidyl ether. In some embodiments, the epoxide is one or more selected from a group including methylstyrene oxides, and ethylene oxide.

In some embodiments, the para-substituted aromatic amine is any para-substituted aromatic amine known in the art. In some embodiments, the para-substituted aromatic amine is one or more selected from a group including aniline, 4-chloroaniline, 4-bromoaniline, 4-iodoaniline, 4-nitroaniline, toluidine, para-anisidine, and 4-aminothiophenol. In some embodiments, the para-substituted aromatic amines may be phenylenediamines. In some embodiments, the mixture has a 1 to 1-5 molar ratio of MOF to para substituted aromatic amine, preferably 1 to 4, 1 to 3, 1 to 2, or 1 to 1.

In some embodiments, the co-catalyst is selected from a group including tetrabutylammonium iodide (TBAI), tetrabutylammonium bromide (TBAB), and tetrabutylammonium fluoride (TBAF). In a preferred embodiment, the co-catalyst is TBAI. In some embodiments, the mixture has a 1 to 100-500 molar ratio, preferably 1 to 150-450, 1 to 200-400, 1 to 250-350, 1 to 300 of co-catalyst to MOF. In an embodiment, the co-catalyst ring opens the epoxide to improve the nucleophilicity of the epoxide towards the $CO_2$.

At step 104, the method 100 includes contacting the mixture with a gas stream containing $CO_2$ to react the $CO_2$ in the gas stream with the epoxide and the para-substituted aromatic amine to form a substituted oxazolidinone mixture. In some embodiments, the gas stream is at least 20 percent by volume (v.%) $CO_2$, preferably at least 30 v.%, 40 v.%, 50 v.%, 60 v.%, 70 v.%, 80 v.%, 90 v.%, or 100 v.% $CO_2$ based on the total volume of the gas stream. In some embodiments, other possible gasses in the gas stream may include but is not limited to, nitrogen, hydrogen, oxygen, water (vapor), carbon monoxide, hydrocarbons having 1-4 carbon atoms (e.g., methane, ethane, ethylene, acetylene, propane, propylene, butane, iso-butane), nitrogen oxides (i.e., nitric oxide, nitrous oxide, nitrogen dioxide), and noble gases (e.g., helium, neon, argon, krypton, xenon), including mixtures thereof. In some embodiments, the $CO_2$ may be sourced from large fossil fuel or biomass electricity power plants, industries with major $CO_2$ emissions, natural gas processing, synthetic fuel plants, and fossil fuel-based hydrogen production plants.

In some embodiments, the method 100 includes contacting the mixture with the gas stream at a temperature of 30-100° C., preferably 40-90° C., 50-80° C., or 60-70° C. In some embodiments, the method 100 includes contacting the mixture with the gas stream at a pressure of 1-15 bar, preferably 3-13 bar, 5-11 bar, or 7-9 bar of the $CO_2$ to form the substituted oxazolidinone mixture. In some embodiments, the method 100 includes contacting the mixture with the gas stream for 5-20 hours, preferably 7-18 hours, 8-16 hours, 10-14 hours or approximately 12 hours, to form the substituted oxazolidinone mixture. In some embodiments, 75-99%, preferably 80-95%, or 85-90% of the para-substituted aromatic amine is converted into the substituted oxazolidinone.

In some embodiments, the substituted oxazolidinone is of formula (II):

where, X is selected from a group including an alkyl chain, an allyloxy group, a halogen substituted alkyl chain, and a substituted aromatic group, and Y is selected from a group including a hydrogen, a halogen, a nitro group, an alkyl chain, a methoxy group, and a thiol. In an exemplary embodiment, the epoxide is 1,2-epoxypropane, the para-substituted aromatic amine is 4-chloroaniline, the co-catalyst is TBAI, and the oxazolidinone of formula (II) is formed wherein X=$CH_3$ and Y=Cl.

In some embodiments, the para substituted aromatic amine is adsorbed to a solid support in the mixture. In an embodiment, the reaction of the $CO_2$, epoxide, and para substituted aromatic amine to form substituted oxazolidinone occurs at the solid support interface, wherein the substituted oxazolidinone remains at least partially on contact with the solid support and/or adsorbed to the solid support, thereby allowing for easy removal and purification from the substituted oxazolidinone mixture. In some embodiments, the solid support is selected from the group consisting of silica gel, alumina, and a polymeric support.

At step 106, the method 100 further includes adding a polar solvent to the substituted oxazolidinone mixture, centrifuging, and filtering to separate recovered MOF and substituted oxazolidinone. In an embodiment, the polar solvent is selected from the group consisting of ethyl acetate, acetone, acetonitrile, dimethylformamide (DMF), dimethylsulfoxide (DMSO), isopropanol, and methanol.

At step 108, the method 100 further includes washing the recovered MOF with an organochloride solvent and drying at a temperature of 130-160° C., preferably 135-155° C., or 140-150° C. for 5 or more hours, preferably 5-12 hours, 6-10 hours, or 7-8 hours to separate recycled MOF. The MOF can be reused in the method 100 without a significant loss in catalytic activity. In some embodiments, the MOF maintains catalytic activity after it is recycled up to 9 times.

EXAMPLES

The following examples describe and demonstrate exemplary embodiments of the method 100 of fixating the $CO_2$ to the substituted oxazolidinone described herein. The examples are provided solely for the purpose of illustration and are not to be construed as limitations of the present disclosure, as many variations thereof are possible without departing from the spirit and scope of the present disclosure.

Materials

Zirconium tetrachloride (99.9% purity), 2,5-dihydroxyterephthalic acid (98% purity), allyl bromide (99% purity), potassium carbonate (99% purity), acetic acid, methanol (99.9% purity), ethanol (97.2% purity), N,N-dimethylformamide (DMF; 99.8% purity), dichloromethane (99.8% extra dry grade), 1,2-epoxypropane (99.5% purity), 1,2-epoxybutane (99.0% purity), 1,2-epoxyhexane (97.0% purity), styrene oxide (97.0% purity), allyl glycidyl ether (99.0% purity), phenyl glycidyl ether (99.0% purity), TBAB (99.0% purity), and TBAI (99.0% purity), aniline (99%) and NMR solvents such as dimethyl sulfoxide-d6 (DMSO-d6; 99.9% purity) and deuterated chloroform ($CDCl_3$) (99.9% purity) were used. Double distilled water filtered through a millipore membrane was used for the study. All chemicals were used without further purification.

Example 1: Method of Rreparation of 2,5-bis (allyloxy)terephthalic Acid Linker ($H_2L$)

Figure 2:
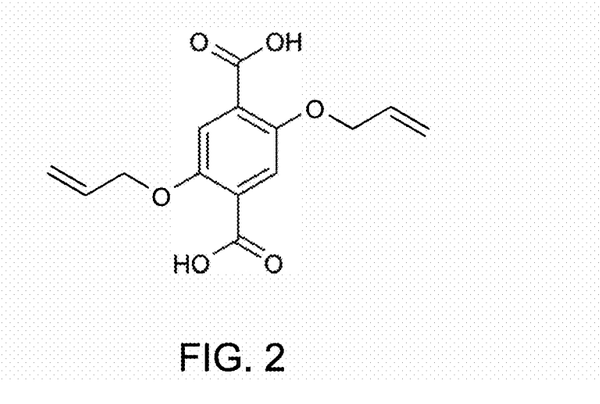
FIG. 2 is a chemical structure of a 2,5-bis(allyloxy) terephthalic acid linker (BAT), according to embodiments of the present disclosure.

Referring to FIG. 2, a chemical structure of 2,5-bis (allyloxy)terephthalic acid linker ($H_2L$) is illustrated. The $H_2L$ was prepared by pre-synthetically modifying the 2,5-dihydroxyterephthalic acid by covalently appending the 2,5-dihydroxyterephthalic acid with allyl group.

Example 2: Synthesis of UiO-66-BAT

Figure 3A:
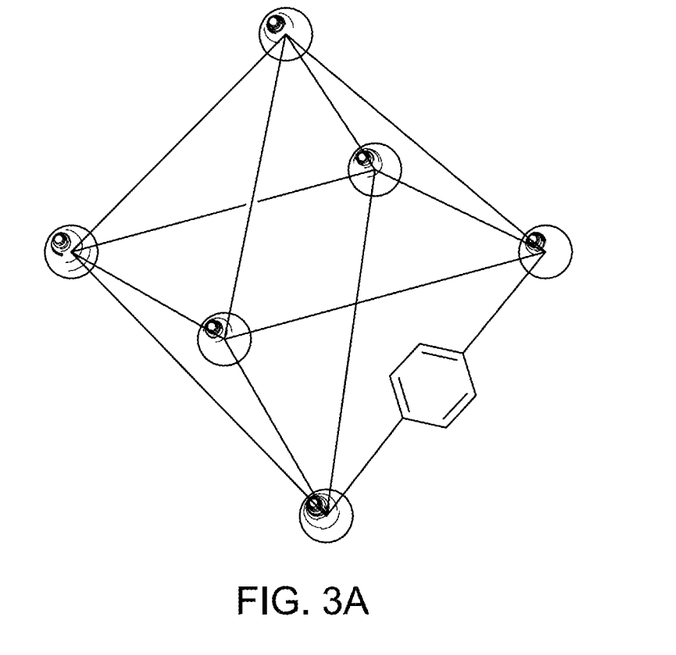
FIG. 3A depicts a schematic presentation of UiO-66, according to embodiments of the present disclosure.
Figure 3B:
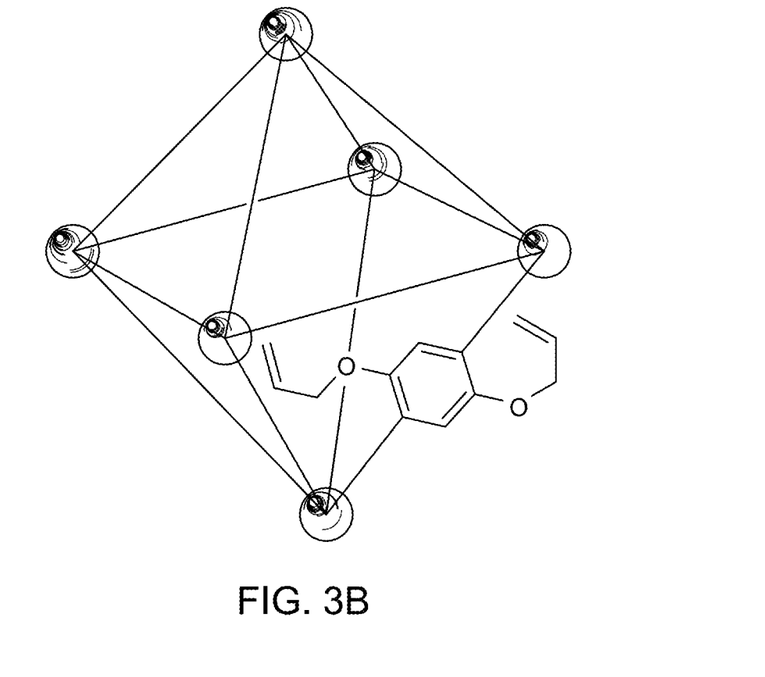
FIG. 3B depicts a schematic presentation of UiO-66-BAT, according to embodiments of the present disclosure.

FIGS. 3A-3B refer to schematic presentations of UiO-66 and UiO-66-BAT, respectively. 116 milligrams (mg) or 0.5 millimole (mmol) of the zirconium tetrachloride and 83 mg or 0.3 mmol of the $H_2L$ was dissolved in 10 milliliters (mL) of DMF and 0.25 mL of acetic acid in a glass vial and heated at 120° C. for 24 hours to form a reaction mixture. The reaction mixture was cooled to room temperature (RT). A slight off-white solid was collected and washed with 3×10 mL of the DMF for three days and 3×10 mL of the methanol for three days yielding the required UiO-66-BAT in 45% yield (related to the zirconium salt). Infrared (IR) (KBr, $cm^{-1}$): 3347, 1667, 1563, 1511, 1442, 1419, 1385, 1362, 1304, 1264, 1212, 1103, 1010, 987, 931, 884, 786, 763. Elemental composition analytically calculated for $C_{90}H_{94}N_2O_{48}Zr_6$ $(Zr_6O_4(OH)_4(C_{14}H_{12}O_6)_6(DMF)_2(H_2O)_2)$: C, 42.91; H, 3.76; N, 1.11; Zr, 21.73; Found: C, 42.50; H, 3.91; N, 1.29; Zr, 21.90.

Example 3: Procedure for $CO_2$ Cycloaddition

The dried UiO-66-BAT (0.1 mmol of Zr), n-tetrabutyl ammonium iodide (TBAI, 37 mg, 0.1 mmol), and an epoxide (5.0 mmol) were added to a 15 mL stainless-steel autoclave and then sealed. The stainless-steel autoclave was operated at a pressure of 5 bar $CO_2$ and heated at 50° C. for 12 hours, followed by cooling and venting of the stainless-steel autoclave. Further, the reaction mixture was diluted with the methanol and centrifuged to separate the catalyst. An organic layer was concentrated and passed through a silica column and eluted with ethyl acetate/hexane mixture. A pure form of respective cyclic carbonates was dried and taken for analysis by $^1H$ Nuclear Magnetic Resonance (NMR) and $^{13}C$ NMR.

Example 4: Procedure for Synthesis of Oxazolidinones From Aromatic Amines, Epoxides, and $CO_2$ 60 mg of the UiO-66-BAT, 10.0 mmol of the epoxide, 2.0 mmol of an aromatic amine and 0.06 mmol of the TBAI were introduced into a 10 mL Schlenk flask. The Schlenk flask was equipped with a balloon of $CO_2$, and a reaction mixture was stirred on a magnetic stirrer at 90° C. for 12 hours. On completion of the present reaction, the reaction mixture was cooled to the RT. The catalyst was separated by centrifugation with the ethyl acetate three times. The combined ethyl acetate layer was concentrated, and a product was isolated by a column chromatography (ethyl acetate/hexane mixture).

Characterization

Analytical thin layer chromatography (TLC) was performed on pre-coated silica gel 60 F254 plates. Visualization of the TLC was achieved by the use of ultraviolet (UV) light (254 nm). Flash column chromatography was undertaken on silica gel (400-630 mesh). Elemental microanalyses (EA) were performed using a PerkinElmer-EA 2400 elemental analyzer. Powdered X-ray diffraction (PXRD) patterns of samples were recorded using a Rigaku MiniFlex diffractometer, which was equipped with Cu-Kα radiation. Data were acquired over two (2) thetas (θ) range of 5° and 30°. Thermogravimetric analysis (TGA) of the samples were performed using a TA Q500. In the present disclosure, an activated sample of the UiO-66-BAT (10 mg) was heated in alumina pan under airflow (60 mL min-1) with a gradient of 10° C. per minute in the temperature range of 30-800° C. Brunauer-Emmett-Teller (BET) surface area of MOFs were calculated by using Micromeritics ASAP 2020 instrument.

Results and Discussion

Figure 4:
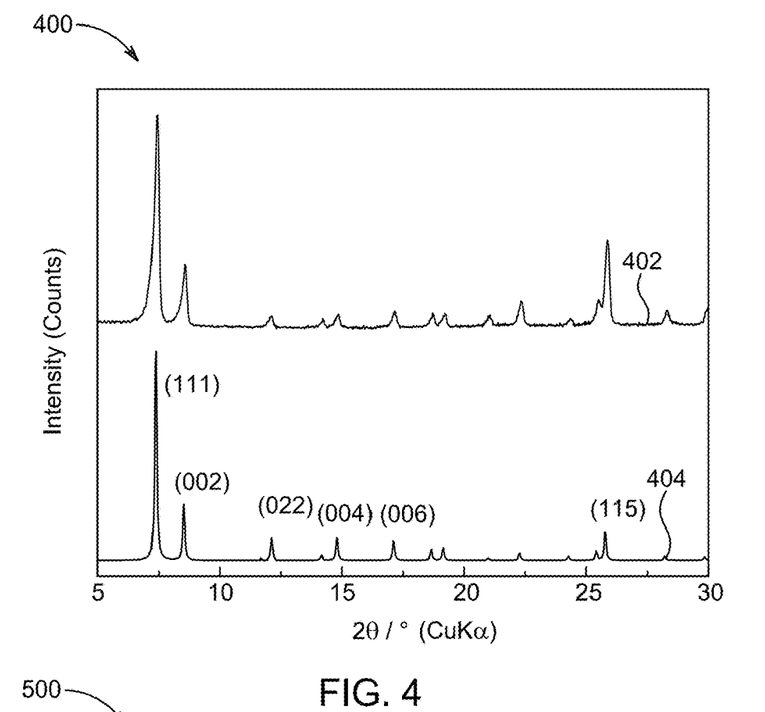
FIG. 4 is a Powdered X-ray Diffraction (PXRD) image of the UiO-66-BAT and the UiO-66, according to embodiments of the present disclosure.

FIG. 4 refers to a PXRD image 400 of the UiO-66-BAT and the UiO-66. The PXRD image includes a first pattern 402 corresponding to the UiO-66-BAT, and a second pattern 404 corresponding to the UiO-66. The first pattern 402 was persistent with the second pattern 404. The UiO-66-BAT showed high crystallinity and identical characteristic peaks of the UiO-66 at 2θ=7.43°, 8.60°. The data as observed in FIG. 4 clearly validates that allyloxy derivatization does not disturb the framework and connectivity of the UiO-66.

Figure 5:
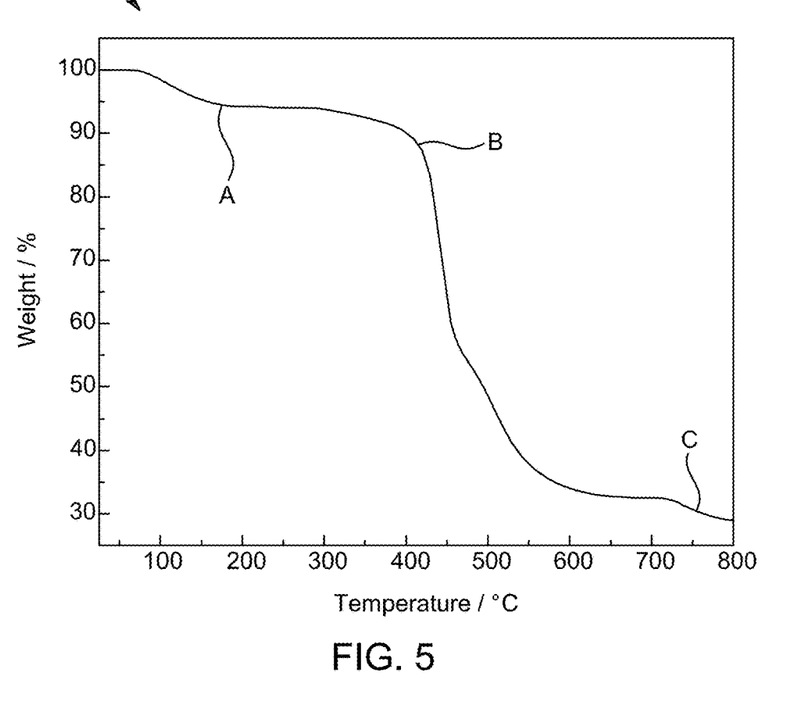
FIG. 5 depicts a thermogravimetric analysis (TGA) of the UiO-66-BAT, according to certain embodiments of the present disclosure.

FIG. 5 is a TGA plot of the UiO-66-BAT. The TGA plot 500 measures the thermal stability of the UiO-66-BAT under an airflow with a heating rate of 5° C. per minute. The TGA plot 500 includes a point 'A' corresponding to an initial mass loss of about 6.0% between 150° C. and 200° C. of the UiO-66-BAT, which is attributed to the evacuation of trapped solvents molecules from pores of a framework. The TGA plot 500 further includes a point 'B' corresponding to a total weight loss of about 64.8% of the UiO-66-BAT which occurs at about 425° C. and is associated with the decomposition of the framework. The point 'B' signifies that the UiO-66-BAT is thermally stable up to 425° C. The TGA plot 500 further includes a point 'C' corresponding to a residue of 29.2%.

Figure 6:
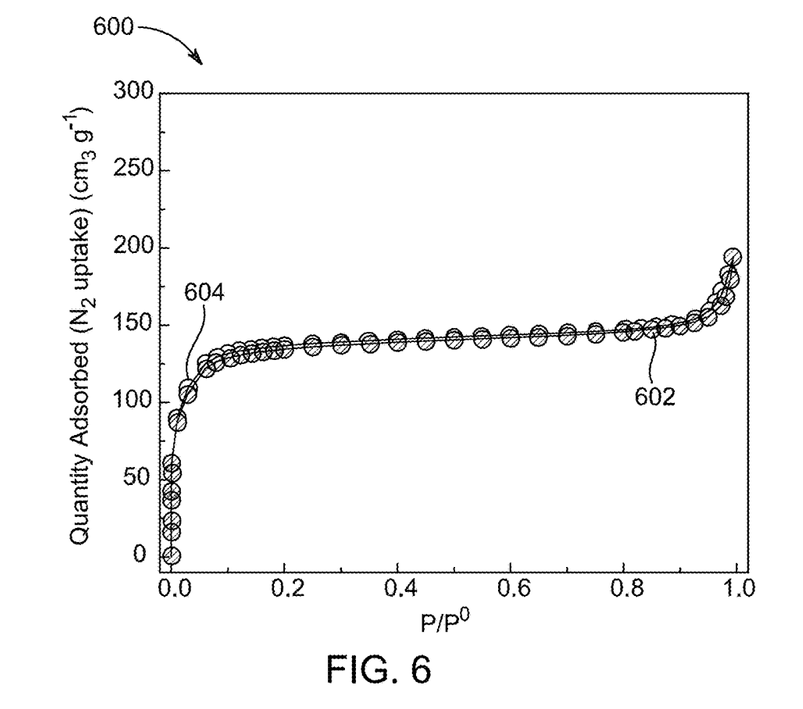
FIG. 6 depicts a nitrogen adsorption isotherm of the UiO-66-BAT according to certain embodiments of the present disclosure.
Figure 7:
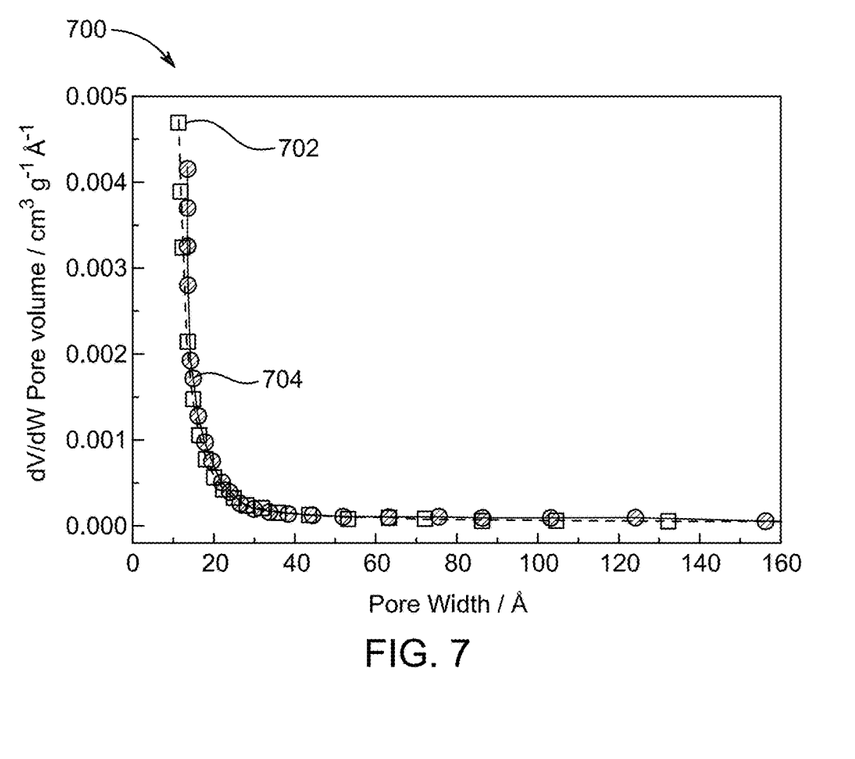
FIG. 7 is Barrett, Joyner, and Halenda (BJH) adsorption pore-size distribution of the UiO-66-BAT and the UiO-66, according to certain embodiments of the present disclosure.

FIG. 6 depicts a nitrogen adsorption isotherm of the UiO-66-BAT. A graph 600 includes a first line 602 corresponding to adsorption of the UiO-66-BAT and a second line 604 corresponding to de-sorption of the UiO-66-BAT. The graph 600 shows type I of the nitrogen sorption experiments of the UiO-66-BAT. The graph 600 further shows significant uptake at relative low pressure (P/PO) of 0 to 0.05 which implies a microporous nature of the UiO-66-BAT. The BET surface area and a pore volume of the UiO-66-BAT was found to be 486 $m^2g^{-1}$. A smaller surface area as compared to the UiO-66 (BET surface area=1167 m2g-1) is attributed to the presence of the appended allyloxy moieties that clog the pores and reduced the surface area. A pore diameter of 1.2 nm was observed for the UiO-66-BAT (702), and about 1.3 nm for the UiO-66 (704), as can be observed from Barrett, Joyner, and Halenda (BJH) adsorption pore-size distribution plot 700 in FIG. 7. The difference in the pore diameter between the UiO-66-BAT (702), and the UiO-66 (704) indicates the presence of allyloxy groups within the pores.

Figure 8:
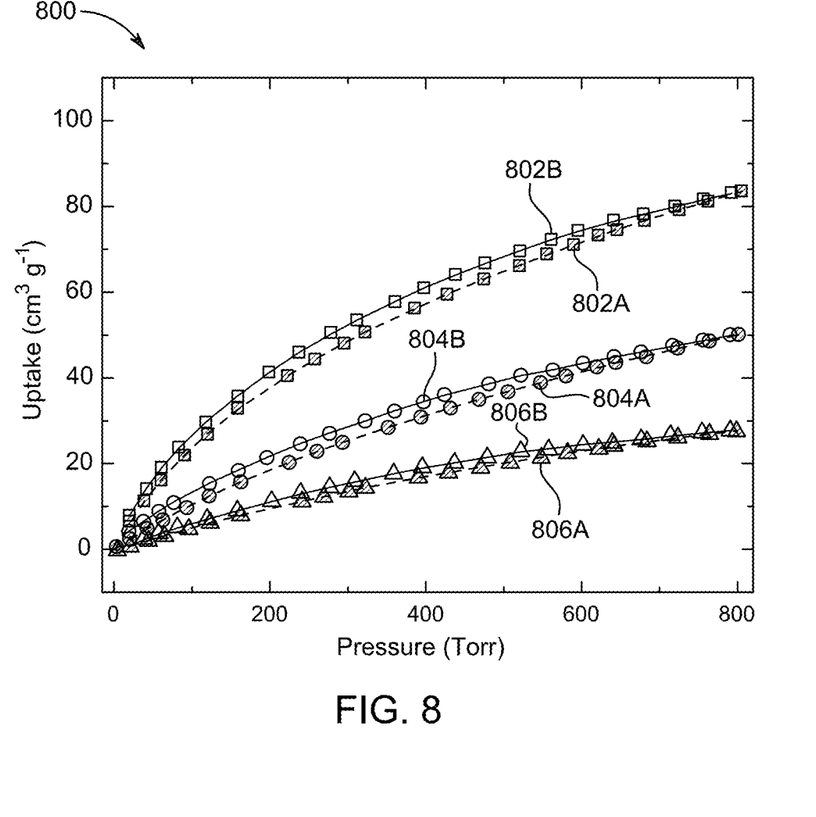
FIG. 8 depicts $CO_2$ isotherms for the UiO-66-BAT at various temperatures, according to certain embodiments.

FIG. 8 depicts a $CO_2$ isotherm plot 800 for the UiO-66-BAT at various temperatures. Adsorption isotherms were measured at different temperatures 298 K (802A), 298 K (804A), and 313 K (806A) over a pressure range of 0-800 torrs, while desorption isotherms were measured at temperatures 298 K (802B), 298 K (804B), and 313 K (806B) over a pressure range of 0-800 torrs. From FIG. 8, it can be observed that the $CO_2$ uptake follows the same decreasing trend with an increase of temperature with the highest uptake of 84 cubic centimeter per gram (cc/g) at 273 K, 51 cc/g at 298 K, and 28 cc/g at 313 K at 800 torrs or 1 bar. To determine the interaction of the allyloxy groups with the $CO_2$ coverage, $CO_2$ adsorption enthalpies of the UiO-66-BAT were determined from the $CO_2$ isotherms collected at 273 K and 298 K upon Clausius-Clapeyron equation. Adsorption enthalpy or isosteric heat of adsorption for the UiO-66-BAT was found to be 27.5 kilojoules per mole (kJ $mol^1$).

Catalysis

Formation of Cyclic Carbonates

Catalytic activities of the UiO-66-BAT was evaluated for the $CO_2$ fixation in the conversion of epoxides to cyclic carbonates. Catalytic activity evaluation studies were carried out using propylene oxide (PO) as a substrate and salt-based co-catalysts in an absence of a solvent. Reactions were carried out in environmentally friendly solvent-free conditions. Process variables such as reaction temperature, pressure, and the catalyst were explored; the results of the present study are shown in Table 1.

TABLE 1

Catalytic activity optimization

| Entry | Catalysts/Co-catalysts | Temperature (° C.) | Pressure (bar) | Yield (%) |
|---|---|---|---|---|
| 1 | — | 80 | 10 | 0 |
| 2 | UiO-66-BAT/— | 80 | 10 | 35 |
| 3 | UiO-66-BAT/TBAI | 80 | 10 | 95 |
| 4 | UiO-66/TBAI | 50 | 5 | 50 |
| 5 | UiO-66-BAT/TBAI* | 50 | 5 | 95 |
| 6 | UiO-66-BAT/TBABr | 50 | 5 | 40 |
| 7 | UiO-66-BAT/TBAF | 50 | 5 | 25 |
| 8 | —/TBAI | 50 | 5 | 15 |

From the Table 1, it can be observed that the yield of the cyclic carbonates at 80° C., reaction time twelve (12) hours, and a pressure of ten (10) bar, was found to be rather low (about 35%), as can be seen from entry 1. Under the same conditions when the co-catalyst TBAI was used, the yield was tremendously increased to 95% (entry 3). The same yield was achieved at a moderate temperature of 50° C., and pressure of 5 bar, and a reaction time of 12 hours (entry 5). 50% yield was achieved when the UiO-66 was reacted under similar conditions. The catalytic activities of the UiO-66-BAT with one or more tetrabutylammonium salts of bromide and fluoride were also evaluated. However, yields were found to be as low as 40% and 25% for the tetrabutylammonium salts of bromide and fluoride, respectively. The condition optimization showed that a reaction duration of 12 hours, at a temperature of 50° C., at a pressure of 5 bar, and catalyst concentration of 2.0 mole % produce the highest conversion from the PO to the corresponding cyclic carbonates.

Further, based on the catalytic performance of the UiO-66-BAT in the conversion of the PO to the corresponding cyclic carbonates, the efficiency of the catalyst was studied with one or more aliphatic and aromatic epoxides, as shown in Table 2.

TABLE 2

Synthesis of cyclic carbonates from one or more epoxides

| Entry | R | Products | Yield[a] (%) |
|---|---|---|---|
| 1 | —CH$_3$ |  | 95 |
| 2 | —CH$_2$CH$_3$ |  | 92 |
| 3 | —CH$_2$CH$_2$CH$_2$CH$_3$ |  | 93 |
| 4 |  |  | 84 |
| 5 |  |  | 91 |
| 6 | —CH$_2$Cl |  | 93 |
| 7 |  |  | 81 |

[a]Reaction conditions: Substrate-10 mmol, catalysts-2 mole %, co-catalyst-1 mole %, reaction time-12 hours, temperature-50° C., pressure-5 bar. Yield was determined from the $^1$HNMR.

Table 2 shows that the UiO-66-BAT can efficiently convert the epoxides to the corresponding cyclic carbonates under a pressure of 5 bar, at 50 oC, and for 8 hours. However, catalytic conversion rates, of PO, butylene oxide, hexylene oxide, allyl glycidyl ether, and epichlorohydrin to cyclic carbonates, are high, which can be attributed to small size of the epoxides, which can penetrate the pores and can easily access active sites (acidic and basic sites) of the catalysts. However, comparatively low conversions were observed for styrene oxide and phenyl glycidyl ether which can be attributed to corresponding bulky structures and steric hindrance toward the active sites of the UiO-66-BAT. In the present catalytic reactions, the cyclic carbonates yield, and purities were confirmed by 1H NMR and 13CNMR analyses of isolated products.

Figure 9:
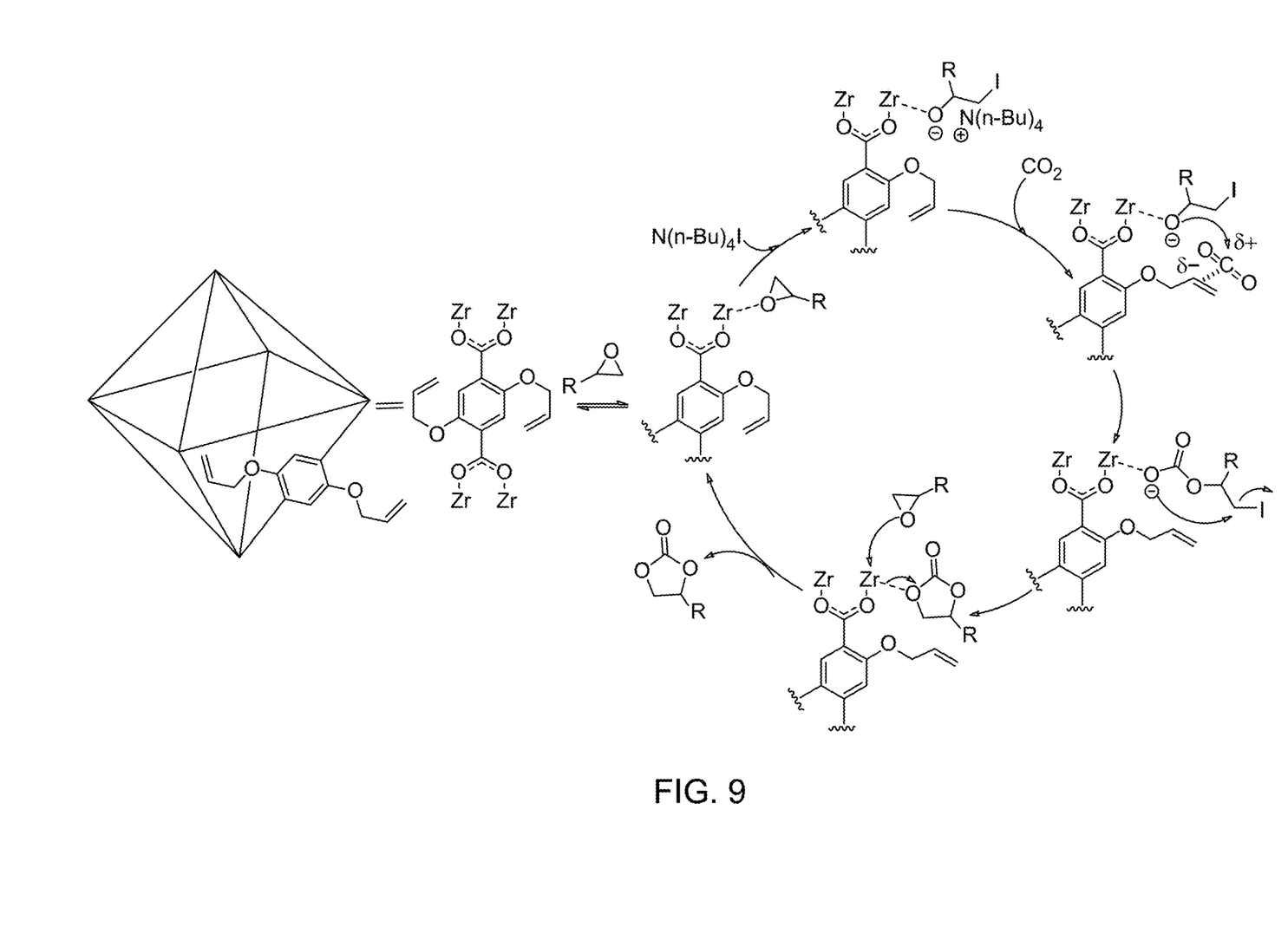
FIG. 9 is a schematic representation depicting a reaction mechanism of a cyclic carbonate formation from an epoxide by the UiO-66-BAT, according to certain embodiments.

FIG. 9 is a schematic representation depicting a reaction mechanism of the cyclic carbonate formation from the epoxide by the UiO-66-BAT. FIG. 9 shows that the epoxide (PO) first binds with a Lewis acidic Zr site through oxygen atom of the epoxide. Bulky iodide ion of the TBAI attacks the less hindered carbon of the epoxide resulting in the opening up of a three-membered epoxide ring, also referred to as the ring. The CO2 molecule polarized by the allyloxy groups of the UiO-66-BAT interact with the oxygen of the opened epoxy ring resulting in the formation of an alkyl carbonate anion. Consequently, the ring closure step results in the formation of the corresponding cyclic carbonates. The cyclic carbonates detach from the Zr resulting in regeneration of the catalysts. Synergistic effect of the allyloxy group and the unsaturated Zr metal clusters of the UiO-66-BAT provided the active sites for the cycloaddition of the $CO_2$ to epoxide to form cyclic carbonates.

Figure 10:
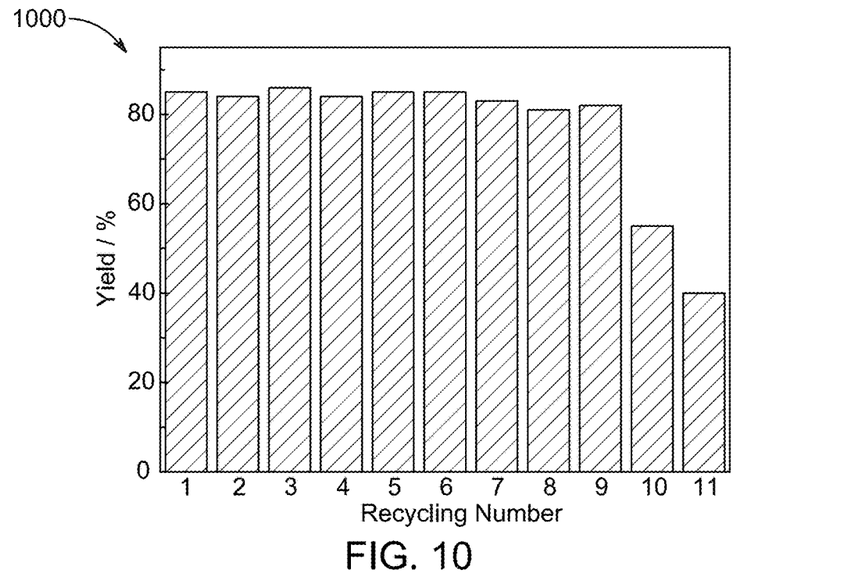
FIG. 10 is a bar-graph depicting the effect on recycling number of the UiO-66-BAT on percentage yield, according to certain embodiments.
Figure 11:
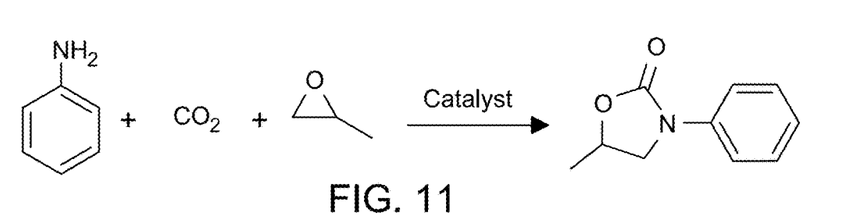
FIG. 11 depicts a reaction of aromatic amines with epoxides in presence of the $CO_2$ to form the oxazolidinone, according to certain embodiments.

FIG. 10 is a bar-graph 1000 depicting recycling number of the UiO-66-BAT as a function of yield. Furthermore, competence of the catalyst was evaluated by recyclability test for the conversion of the PO to the corresponding cyclic carbonates. After completion of a reaction of FIG. 9, reaction mixture was diluted with MeOH, and the catalysts were recovered by simple centrifugation at 5000 rotations per minute (rpm). Recovered UiO-66-BAT was repeatedly washed with dichloromethane 10 mL (to remove remaining PO, TBAI, and product) three times and chloroform 10 mL (three times), and then dried under vacuum overnight. The UiO-66-BAT exhibited efficient conversion up to nine cycles without the loss of the framework. Formation of oxazolidinone from aromatic amines, epoxides, and $CO_2$ A reaction (FIG. 11) of the aniline, 1,2-epoxypropane, and $CO_2$ with the UiO-66-BAT determined the catalytic activity of the UiO-66-BAT. The catalytic activities of the UiO-66-BAT with one or more tetrabutylammonium salts of bromide, chloride, and fluoride were studied, however, corresponding yields were as low as 41%, 29%, and 13%, respectively than the TBAI (90%). The present results can be ascribed to an efficient leaving group and a nucleophilic nature of the iodide ion compared to the bromide, chloride and fluoride ions that enable the TBAI to enhance the reaction rate.

Further, results of cycloaddition reactions of the $CO_2$ with one or more aromatic amines and the 1,2-epoxypropane in presence of the UiO-66-BAT as catalysts are shown in Table 3.

TABLE 3

Cycloaddition reaction of the $CO_2$ with one or more aromatic amines (A1-A6) and the 1,2-epoxypropane in presence of the UiO-66-BAT as the catalyst[a].

| Entry | Aromatic Amine | Product | Yield (%)[b] |
|---|---|---|---|
| 1 | aniline (A1) | C1 | 90 |
| 2 | 4-nitroaniline (A2) | C2 | 95 |
| 3 | 4-methylaniline (A3) | C3 (H₃C—C₆H₄—NH₂) | 79 |
| 4 | 4-methoxyaniline (A4) | C4 | 85 |

TABLE 3-continued

Cycloaddition reaction of the $CO_2$ with one or more aromatic amines (A1-A6) and the 1,2-epoxypropane in presence of the UiO-66-BAT as the catalyst[a].

| Entry | Aromatic Amine | Product | Yield (%)[b] |
|---|---|---|---|
| 5 | A5 (4-chloroaniline) | C5 | 93 |
| 6 | A6 (4-aminothiophenol) | C6 | 71 |

[a]Reaction conditions: 1,2-epoxypropane (10.0 mmol), aromatic amine (2.0 mmol), solvent-free, catalyst (60 mg), $CO_2$ (1 bar), 12 h, 90° C., TBAI as the co-catalyst.
[b]Isolated yield calculated with respect to A. Determined by $^1H$ NMR spectroscopy. Products of Table 3 had 100% selectivity.

Table 3 shows that the aniline with an electron-withdrawing group such as (—$NO_2$) and (—Cl) gave a higher yield of 95% and 93% respectively (Entry 2, and 5) as compared to the aniline with electron-donating group (—$CH_3$ yield 79%, —$OCH_3$ yield 85%, and —SH yield 71%) (Entry 3, 4, and 6). Further, the catalyst's applicability was also checked with one or more epoxides (B2-B7) and outcome is summarized in Table 4.

TABLE 4

Cycloaddition reaction of the $CO_2$ with one or more epoxides and the aniline in presence of the UiO-66-BAT as the catalyst.[a]

| Entry | Epoxides | Product | Yield (%)[b] |
|---|---|---|---|
| 1 | B2 | C7 | 88 |
| 2 | B3 | C8 | 87 |
| 3 | B4 | C9 | 89 |
| 4 | B5 | C10 | 75 |

TABLE 4-continued

Cycloaddition reaction of the CO₂ with one or more epoxides and the aniline in presence of the UiO-66-BAT as the catalyst.[a]

| Entry | Epoxides | Product | Yield (%)[b] |
|---|---|---|---|
| 5 |  B6 |  C11 | 77 |
| 6 |  B7 |  C12 | 65 |

[a]Reaction conditions: Epoxides (10.0 mmol), aniline (2.0 mmol), solvent-free, catalyst (60 mg), CO₂ (1 bar), 12 h, 90° C., TBAI as the co-catalyst.
[b]Isolated yield calculated with respect to A. Determined by ¹H NMR spectroscopy. Products in Table 4 had 100% selectivity.

Table 4 shows that monosubstituted aliphatic (B2-B4) and aromatic epoxides gave a high yield of 90-87% of the oxazolidinone with the aniline. The reaction proceeded efficiently with bulky disubstituted epoxides such as cyclohexane oxide in the presence of the UiO-66-BAT giving the corresponding oxazolidinone in 65% yield (B7). The catalyst UiO-66-BAT leads to the formation of only 5-substituted oxazolidinones and not 4-substituted oxazolidinones or a mixture of two, preferably as a result of steric hindrance between the aromatic amines, epoxide side chain, and the framework of the UiO-66-BAT. The product was characterized by ¹H NMR and ¹³C NMR spectra, and the identities of the oxazolidinones were confirmed by correlation with literature.

Figure 12:
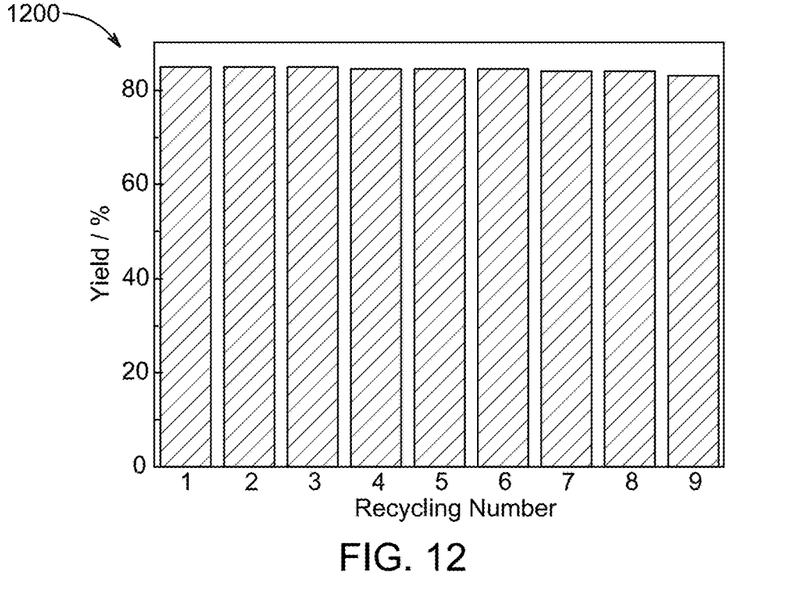
FIG. 12 is a bar-graph depicting recycle tests with the UiO-66-BAT for a reaction of the $CO_2$ with aniline and 1,2-epoxypropane to form an oxazolidinone, according to certain embodiments.

Further, FIG. 12 is a bar-graph 1200 depicting recycle tests with the UiO-66-BAT for the reaction of the CO₂ with the aniline and 1,2-epoxypropane to form the oxazolidinone. Recyclability is an essential aspect of heterogeneous catalysis. The UiO-66-BAT can be efficiently recovered after completion of the reaction from the reaction mixture by centrifugation and then wash with the DMF and dichloromethane consecutively three times each. The catalysts were again activated by heating the MOF at 150° C. in a vacuum oven for 6 hours. Recycle performance of the UiO-66-BAT for the reaction between the epoxide, aniline and CO₂ was studied, which confirmed that the UiO-66-BAT could be reused for nine cycles without any noticeable loss in catalytic activity.

The catalyst of the present disclosure (UiO-66-BAT) provides efficient separation, sample handling, and reusability. The UiO-66-BAT includes a porous structure, efficient adsorption properties, a robust framework, thermal and chemical stability, tunable properties, and high surface area. Furthermore, the allyloxy groups of the UiO-66-BAT have an efficient affinity towards the CO₂. Moreover, the allyloxy groups covalently bonded to the framework of the MOF, which can swivel and rearrange within the pores to interact with the CO₂ to have a solvation-like effect. Formation of the cyclic carbonates by the CO₂ fixation with the epoxides provide an atom-economical chemical reaction. The cyclic carbonates can be used as aprotic, polar, and nonflammable solvents in several reactions. Further, the cyclic carbonates can be precursors for synthesis of polycarbonates and can also act as intermediates in several organic reactions and as electrolytes for industrial processes. Furthermore, the oxazolidinones can be used as intermediates in one or more organic synthesis, as antibacterial, antimicrobial agents such as tedizolid, linezolid, and radezolid, and can also act as structural units in pharmaceutical and agrochemical industries.

Obviously, numerous modifications and variations of the present disclosure are possible in light of the above teachings. It is therefore to be understood that within the scope of the appended claims, the invention may be practiced otherwise than as specifically described herein.

The invention claimed is:
1. A method of fixating carbon dioxide (CO₂) to a substituted oxazolidinone, comprising:
    mixing a metal-organic framework (MOF), a co-catalyst, at least one para-substituted aromatic amine, and at least one epoxide to form a mixture; and
    contacting the mixture with a gas stream containing CO₂ to react the CO₂ in the gas stream with the epoxide and the para-substituted aromatic amine to form a substituted oxazolidinone mixture;
    wherein the MOF is a UiO-66-X MOF;

wherein X is of formula (I):

(I)

wherein:
at least one of $R^1$ to $R^4$ is an allyloxy group; and
$R^1$ to $R^4$ are independently an allyloxy group or a hydrogen.

2. The method of claim 1, wherein:
X is:

3. The method of claim 1, wherein the MOF has:
a surface area is 450-550 square meter per gram ($m^2/g$).

4. The method of claim 1, wherein the MOF has:
a pore size of 1.0-1.5 nanometers (nm).

5. The method of claim 1, wherein the MOF has:
a $CO_2$ uptake capacity of 75-90 cubic centimeter per gram ($cm^3/g$) at 273 kelvin (K), 40-60 $cm^3/g$ at 298K, and 20-35 $cm^3/g$ at 313K, each at 800 torr.

6. The method of claim 1, wherein:
the epoxide is at least one selected from a group consisting of 1,2-epoxypropane, 1,2-epoxybutane, 1,2-epoxyhexane, styrene oxide, allyl glycidyl ether, and phenyl glycidyl ether.

7. The method of claim 1, wherein:
the para-substituted aromatic amine is at least one selected from a group consisting of 4-chloroaniline, 4-nitroaniline, toluidine, para-anisidine, and 4-aminothiophenol.

8. The method of claim 1, wherein:
the co-catalyst is selected from a group consisting of tetrabutylammonium iodide (TBAI), tetrabutylammonium bromide (TBAB), and tetrabutylammonium fluoride (TBAF).

9. The method of claim 1, wherein:
the mixture has a 1 to 100-500 molar ratio of the co-catalyst to the MOF.

10. The method of claim 1, wherein:
the mixture has a 1 to 1-5 molar ratio of the MOF to the para-substituted aromatic amine.

11. The method of claim 1, wherein the para-substituted aromatic amine is adsorbed to a solid support in the mixture.

12. The method of claim 11, wherein the solid support is selected from a group consisting of silica gel, alumina, and a polymeric support.

13. The method of claim 1, wherein the contacting occurs at a temperature of 30-100 degrees Celsius (° C.).

14. The method of claim 1, wherein the contacting occurs at a pressure of 1-15 bar of the $CO_2$.

15. The method of claim 1, wherein the contacting occurs for 5-20 hours.

16. The method of claim 1, wherein:
75-99% of the para-substituted aromatic amine is converted into the substituted oxazolidinone.

17. The method of claim 1, wherein:
the substituted oxazolidinone is of formula (II)

(II)

wherein:
X is selected from a group consisting of an alkyl chain, an allyloxy group, a halogen substituted alkyl chain, and a substituted aromatic group; and
Y is selected from a group consisting of a halogen, a nitro group, an alkyl chain, a methoxy group, and a thiol.

18. The method of claim 1, further comprising:
adding a polar solvent to the substituted oxazolidinone mixture, centrifuging, and
filtering to separate recovered MOF;
washing the recovered MOF with an organochloride solvent and drying at a temperature of 130-160° C. for at least 5 hours to separate recycled MOF.

19. The method of claim 18, wherein:
the MOF maintains catalytic activity after it is recycled up to 9 times.

* * * * *